United States Patent [19]

Vega

[11] Patent Number: 4,750,831
[45] Date of Patent: Jun. 14, 1988

[54] APPARATUS AND METHOD FOR SELF-EXAMINATION OF THE EYE AND SURROUNDING FACIAL AREAS

[76] Inventor: L. Eduardo Vega, 420 S. Essex La., Tucson, Ariz. 85711

[21] Appl. No.: 867,242

[22] Filed: May 23, 1986

[51] Int. Cl.$^4$ ............................ A61B 3/02; G02B 5/08
[52] U.S. Cl. ...................................... 351/223; 350/621
[58] Field of Search ............... 351/223, 247, 200, 222; 350/442, 641, 600, 621

[56] References Cited
U.S. PATENT DOCUMENTS

| | | | |
|---|---|---|---|
| 2,135,743 | 11/1938 | Cassity | 351/205 |
| 2,582,227 | 1/1952 | Brady | 351/223 |

Primary Examiner—Rodney B. Bovernick
Assistant Examiner—P. M. Dzierzynski
Attorney, Agent, or Firm—Harry M. Weiss & Assoc.

[57] ABSTRACT

A self-examination apparatus for the eye and the surrounding facial area is described in which a lens supported by housing can be moved with relation to the observer to provide a detailed or amplified image of the eye. The housing includes a substantially extended member for preventing sunlight from inadvertently being reflected off the lens into the observer's eye. The examination system further includes a self-illumination system that can provide the illumination when ambient conditions will not provide sufficient illumination for self-examination.

6 Claims, 2 Drawing Sheets

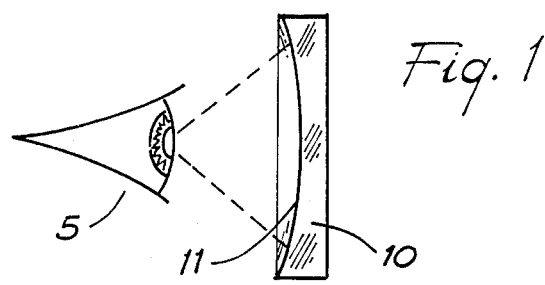
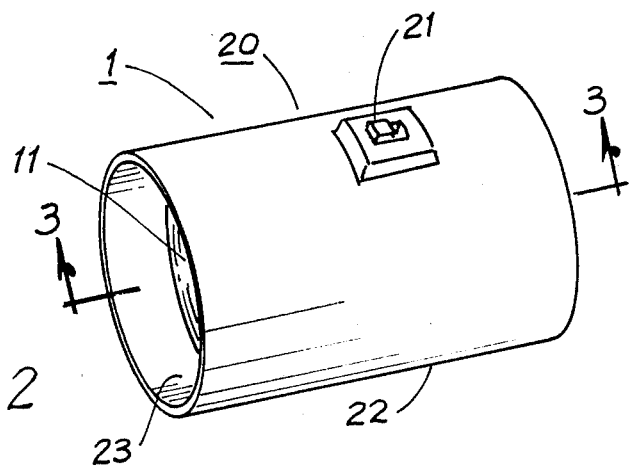
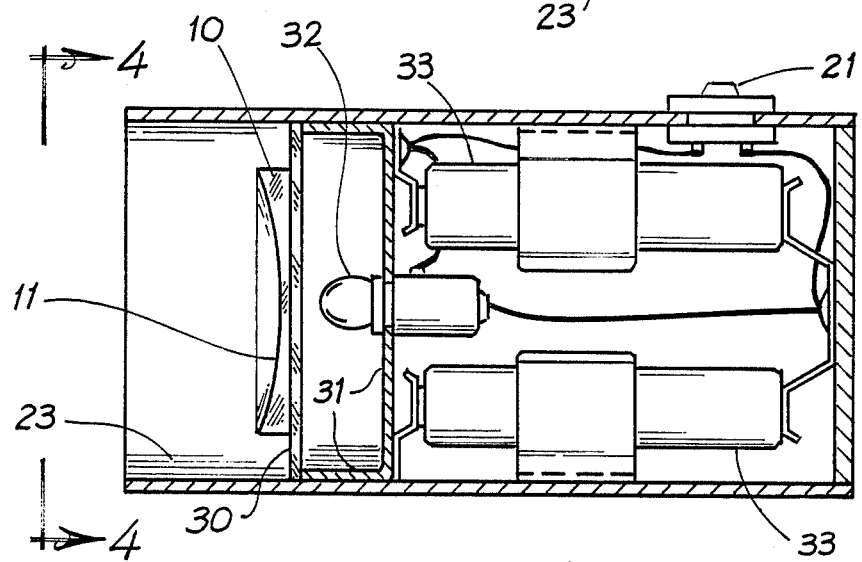
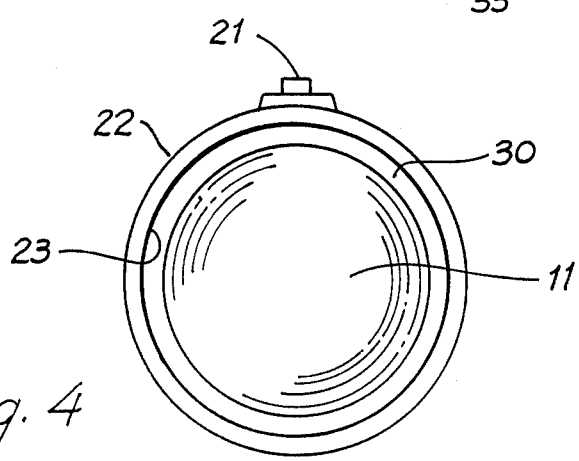

APPARATUS AND METHOD FOR SELF-EXAMINATION OF THE EYE AND SURROUNDING FACIAL AREAS

BACKGROUND OF THE INVENTION

1. Field of the Invention

This invention relates generally to optical systems and more particularly, to an optical system for detailed self-analysis of the eye and surrounding regions of the face.

2. Description of the Related Art

It has been known in the prior art to examine the eye and surrounding area by use of a mirror. However, it has been found that the use of an ordinary mirror for such examination is not suitable for detailed investigation involving the eye, particularly with respect to the use of contact lenses. For the person who uses a contact lens, it is necessary to appraise the accuracy of the positioning of the lens over the cornea to visualize the presence or absence of any air bubbles, dirt particles, eye lashes, etc., that may cause discomfort, visualize the presence or absence of any folds or tears of the soft lens or any fractures or defects in a hard contact lens, and adjust the position of the so-called bifocal contact lens which requires that a specific portion of the lens be situated over the lower part of the cornea at all times. Such activity requires a closer examination of the eyeball than has typically been available through the use of an ordinary mirror.

It has been known in the prior art to use a concave lens for the entire facial examination. Such lenses are typically found in dressing areas and can be used for the application of cosmetics and for other activity requiring a somewhat more detailed visual image of the facial region than can be provided by use of a mirror. Typically, however, such concave lenses have not been satisfactory to provide a detailed examination of the specific area such as the area of the eye. In addition, such lenses have typically been fairly large and therefore have not been suitably portable. Also, the focal lengths of said lenses do not permit close examination of the eye.

It is therefore an object of the present invention to provide an optical system that is easily portable and which can be used to provide a detailed self-examination of the area of the eye or surrounding facial regions. In addition, it is desirable to provide a self-examination instrument that does not rely on ambient light and yet can protect against inadvertent focussing of direct sunlight to the eye or other parts of the face and body.

SUMMARY OF THE INVENTION

It is therefore an object of the present invention to provide apparatus and method for detailed examination of the eye and surrounding facial region.

It is a more particular object of the present invention to provide an apparatus for detailed examination of the area of the eye that includes a lens system for close examination of the view area.

It is a more particular object of the present invention to provide apparatus and method for detailed examination of the area of the face in the vicinity of the eye that provides a self-contained source of illumination.

It is yet another object of the present invention to provide an apparatus and method for detailed self-examination in the vicintiy of the eye that can protect against inadvertent exposure to direct sunlight.

The aforementioned and other objects of the present invention are accomplished, according to the present invention, by providing a housing that holds a lens. The lens can be positioned by the user to provide a detailed image to the user of the area under examination. In addition, the holder has a surface extending beyond the lens surface which minimizes the risk of reflection of direct sunlight into the eye. The holder also includes a lamp and battery system along with a switch for activating and deactivating the lamp that provides illumination of the area under examination.

These and other features of the present invention will be understood upon reading of the following descriptio along with the drawings.

BRIEF DESCRIPTION OF THE DRAWINGS

FIG. 1 is a schematic representation of the use of a lens for detailed examination.

FIG. 2 is a perspective view of the self-examination apparatus of the present invention.

FIG. 3 is a cross-section view, taken along line 3—3 of FIG. 2, of the apparatus according to the present invention for examination of the area of the eye.

FIG. 4 is a front view of the apparatus for facial self-examination of the present invention.

DESCRIPTION OF THE PREFERRED EMBODIMENT

Detailed Description of the Figures

Figure 5:
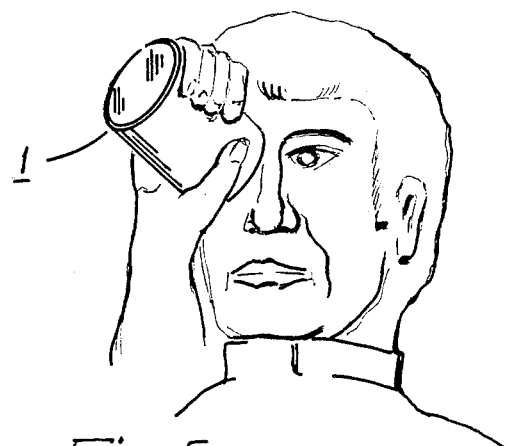
FIG. 5 is a view further showing the apparatus of the present invention in use.

Referring first fo FIG. 1, and FIG. 5 the basic optical configuration of the self-examination apparatus of the present invention, generally referred to by reference number 1, is shown in use. The eye 5 uses a lens system 10 that includes a reflecting concave surface 11 or any other type of reflecting surface 12, such as convex surface 12 shown in FIGS. 6 and 7. By varying the position of the eye 5 and the lens system 10, a close visualization of the image of the eye 5 can be obtained. It will be clear that the radius of curvature of the concave surface 11, for example, will determine the optimum viewing distance of the eye for self-examination of the eye. Other reflective convex lens surface 12, or the like may be used and having similar results as the above-discussed concave surface 11.

Figure 6:
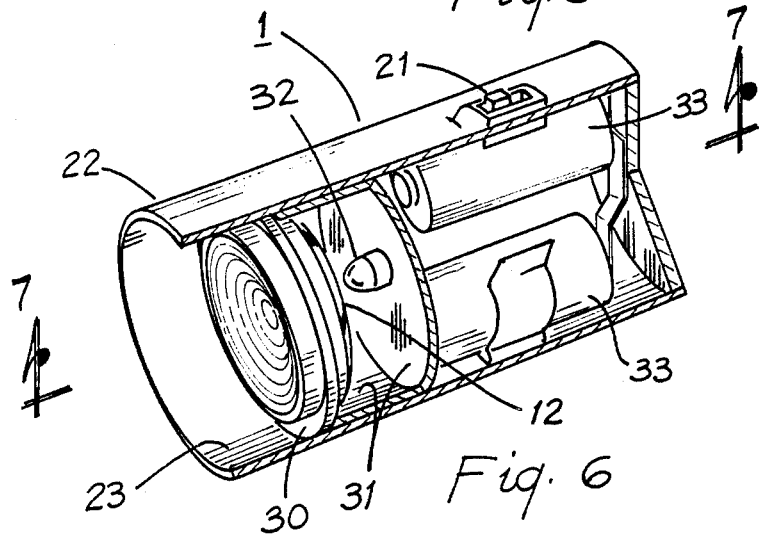
FIG. 6 is a perspective view showing a partial cutaway showing the elements of the present invention with a convex lens reflecting surface.

Referring next to FIG. 2, and FIG. 6, there is shown, in perspective views, the self-examination apparatus 1 of the present invention, including the optical system and associated apparatus. The apparatus comprises a housing 20 that includes an outer surface 22 and a switch 21 positioned on the outer surface 22. The concave surface 11, (see FIG. 2) or other reflecting lens surface 12, (see FIG. 6) is positioned such that a highly reflective inner wall 23 extends beyond the lens system.

Figure 7:
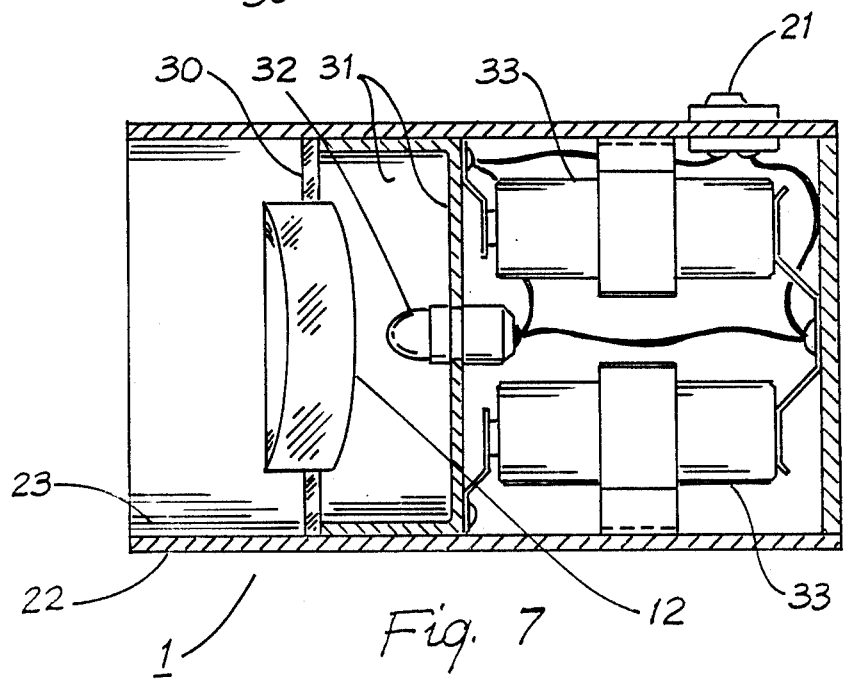
FIG. 7 is a cross-section view, taken along line 7—7 of FIG. 6, showing a convex lens reflecting surface arrangement of the present invention.

FIG. 3 shows a cross-sectional view taken along the line indicated 3—3 in FIG. 2, wherein lens system 10 is shown as a concave reflective surface 11. Similarly, FIG. 7 shows a cross-sectional view taken along the line indicated 7—7 in FIG. 6, wherein lens system 10 is shown as a convex reflective lens surface 12. FIGS. 3 and 7 further showing wall portion 23 of housing 20 extending well beyond lens system 10. Shown also in FIGS. 3 and 7 is lens system 10 mounted on a transparent member 30 and having lightbulb 32 being located there behind lens system 10 in a highly reflective chamber 31. interior of the housing behind the reflecting chamber 31 includes batteries 33 and associated electrical couplings 28 and springs 29 for mounting the batteries 33 and for coupling the batteries 33 and the light bulb 32 with switch 21. Through switch 21, the light bulb 32 can be activated as needed.

Referring next to FIG. 4, a front view of the self-examination apparatus 1 is shown. The outer surface of the housing is 22, the inner surface of the extended region of the housing is shown as 23, while the lens system 10 and the transparent member 30 are positioned in the interior of the extended portion 23. Also shown is switch 21 for activating the light bulb 32.

Operation of the Preferred Embodiment

The self-examination apparatus 1 is adapted to have a reflecting surface 11, 12 of the lens system (preferably concave, although other reflecting shapes may be used as previously discussed) by which the eye 5 can see an exquisitely detailed version of itself by looking into the lens system 10. The apparatus 1 includes a shield 23 that prevents direct sunlight from inadvertently striking the reflecting surface 11, 12 and being reflected toward the region of the eye 5, possibly damaging the eye 5. In addition, the self-examination apparatus 1 has an independent light source (e.g., lightbulb 32) so that in low levels of ambient light, the user will not be viewing the image at a low level of illumination. The lightbulb 32 is adapted to provide light that exits from the surface 31 of the lamp chamber through the transparent member 30 and forwardly onto the region of the eye as well as onto the extended wall portions 23. The extended wall portions 23 of the housing 23 are highly reflective so that a large percentage of the light is projected forward and into the region of the eye 5.

It will be clear to those skilled in the art that the reflective surface 11, 12 is located on the outside of lens system 10 of the preferred embodiment. However, said reflective surface 11, 12 can be located elsewhere in the lens system 10.

A use of the self-examination apparatus 1 previously discussed, is to assist people in adjusting contact lenses. Because of the nature of the contact lens, as well as its small size, the present invention provides an improved method for manipulation of said contact lens.

In addition, the self-examination apparatus 1 has further applications to ophtalmological and related activities in which a patient can be expected to provide self-examination. The apparatus 1 permits the user to see in detail the characteristics of the cornea and the conjutiva, the anterior chamber, the iris pupil, lens and surrounding tissue. Also various parts of the eyelids and associated structures can be examined. Examples of further uses can be visualization of the location of eye damage produced by a foreign object of examination of changes related to inflammatory or infectious diseases of the eyes and surrounding tissues and the evolution and progression of diseases of the lenses such as cataracts. In addition, many useful applications can be derived in indentifying and monitoring changes related to therapeutic modalities as they affect the eye and the surrounding tissues. the changes produced by therapy including surgical therapy of various diseases and tumorous conditions of the eyes can be monitored by the patient. The device can be of assistance for the patient in seeing details of the results of plastic surgery and other changes in the vicinity of the eye such as reconstructive procedures.

The present invention also permits a close inspection of the eyelids and surrounding areas that can be used to insure the correct usage of makeup and similar modalities of said surrounding areas and to insure complete removal of makeup after cleaning or washing of the area. Consequently, the self-examination apparatus 1 can be especially important in identifying the presence of irritating makeup residuals in the connecting areas of the eye 5. The self-examination apparatus 1 can also be used to examine tattoos of the eyelid areas or by those attempting to provide their own tattoo procedures on the surrounding area of the eye 5.

While the invention has been particularly shown and described in reference to preferred embodiments thereof, it will be understood by those skilled in the art that changes in form and details may be made without departing from the spirit and scope of the invention.

I claim:

1. An apparatus for self-examination of a user's eye and surrounding facial area, said apparatus comprising:
   (a) a housing means for encasing said apparatus, said housing means having a hooded front portion provided with reflective inner walls;
   (b) a lens means for reflecting images of said user's eye and surrounding facial area, said lens means being supported within said housing means, said hooded front portion extending beyond the location of said lens means and thereat shielding said user's eye and surrounding facial area from extraneous light when said apparatus is being used;
   (c) a transparent member means for supporting said lens means within said housing means and for transmitting light through an area overlapping and surrounding said lens means;
   (d) a light means for illuminating a user's eye and surrounding facial area;
   (e) a reflecting chamber means for reflecting light forwardly from said light means, said light being reflected forwardly through said transparent member, partially onto said user's eye and surrounding facial area and partially onto said reflective inner walls of said hooded front portion and then onto said user's eye and surrounding facial area;
   (f) a power source means for energizing said light means; and
   (g) a switch means for powering on and off said light means, said switch means being mounted onto an exterior portion of said housing means.

2. The apparatus for self-examination as in claim 1 wherein:
   said lens means has an anterior reflective surface which is substantially configured as concave.

3. The apparatus for self-examination as in claim 1 wherein:
   said lens means has a posterior reflective surface which is substantially configured as convex.

4. A method for self-examination of a user's eye and surrounding facial area, comprising the steps of:
   (a) positioning a self-examining apparatus proximate said user's eye and surrounding facial area, said self-examining apparatus including a housing, said housing further including a light means for illuminating said user's eye and surrounding facial area, a light reflecting chamber, a transparent member means for transmitting light from said reflecting chamber, a lens means for reflecting images, and a hooded portion having reflective inner walls located frontally of said lens means;

(b) energizing said light means;

(c) illuminating said light reflecting chamber;

(d) transmitting light from said light reflecting chamber forwardly through said transparent member means, then onto said reflective inner walls of said hooded portion;

(e) illuminating said user's eye and surrounding facial area using said transmitted light on said reflective inner walls of said hooded portion;

(f) shielding extraneous light from said user's eye and surrounding facial area using said hooded portion;

(g) selecting an examination point on said user's eye and surrounding facial area;

(h) projecting images of said selected examination point onto said lens means;

(i) reflecting said projected images from said lens means; and (j) viewing and examining said reflected images of said user's eye and surrounding facial area.

5. The method for self-examination of a user's eye and surrounding facial area as in claim 4 wherein:
said lens means has an anterior reflective surface which is substantially configured as concave.

6. The method for self-examination of a user's eye and surrounding facial areas as in claim 4 wherein:
said lens means has a posterior reflective surface which is substantially configured as convex.

* * * * *